US009080158B2

(12) United States Patent
Takano et al.

(10) Patent No.: US 9,080,158 B2
(45) Date of Patent: *Jul. 14, 2015

(54) METHOD OF PRODUCING S-ADENOSYL-L-METHIONINE-CONTAINING DRY YEAST HAVING EXCELLENT STORAGE STABILITY, THE PRODUCT THEREOF AND COMPOSITION FOR ORAL INTAKE

(75) Inventors: Kentarou Takano, Niigata (JP); Shinyo Gayama, Niigata (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 1087 days.

This patent is subject to a terminal disclaimer.

(21) Appl. No.: 12/300,826

(22) PCT Filed: May 15, 2007

(86) PCT No.: PCT/JP2007/059917
§ 371 (c)(1),
(2), (4) Date: Nov. 14, 2008

(87) PCT Pub. No.: WO2007/132831
PCT Pub. Date: Nov. 22, 2007

(65) Prior Publication Data
US 2009/0186400 A1    Jul. 23, 2009

(30) Foreign Application Priority Data

May 16, 2006  (JP) .................................. 2006-135957

(51) Int. Cl.
| | |
|---|---|
| *C12N 1/12* | (2006.01) |
| *C12N 1/20* | (2006.01) |
| *A01N 63/00* | (2006.01) |
| *C12N 1/18* | (2006.01) |
| *A61K 9/16* | (2006.01) |
| *A61K 9/19* | (2006.01) |
| *C07H 19/167* | (2006.01) |
| *C12N 1/04* | (2006.01) |
| *C12P 19/40* | (2006.01) |

(52) U.S. Cl.
CPC ................. *C12N 1/18* (2013.01); *A61K 9/1617* (2013.01); *A61K 9/19* (2013.01); *C07H 19/167* (2013.01); *C12N 1/04* (2013.01); *C12P 19/40* (2013.01)

(58) Field of Classification Search
CPC .............. A61K 2300/00; A61K 31/35; A61K 31/7076; A61K 36/06; A23V 2002/00; C12N 15/81; C12N 1/16; C12N 1/18; C12N 1/04; C12P 17/12; C12P 17/182; C12P 19/40; C12P 13/04; C12P 17/18; A23K 1/1853; A23L 1/3016
See application file for complete search history.

(56) References Cited

U.S. PATENT DOCUMENTS

| | | | |
|---|---|---|---|
| 4,677,073 | A | 6/1987 | Grabitz |
| 4,851,390 | A * | 7/1989 | Morishige ................... 514/44 R |
| 6,881,837 | B2 | 4/2005 | Deshpande et al. |
| 8,202,515 | B2 | 6/2012 | Takano et al. |
| 2007/0082112 | A1* | 4/2007 | Kincs et al. ................... 426/601 |

FOREIGN PATENT DOCUMENTS

| | | |
|---|---|---|
| EP | 0 072 980 A1 | 3/1983 |
| EP | 0 073 376 A1 | 3/1983 |
| EP | 0 141 914 A1 | 5/1985 |
| EP | 0 162 323 A1 | 11/1985 |
| EP | 0 189 322 A2 | 7/1986 |
| EP | 0 659 344 A1 | 6/1995 |
| EP | 1 091 001 A1 | 4/2001 |
| FR | 1509676 | 1/1967 |
| GB | 1064212 B1 | 4/1967 |
| JP | 45-033753 | 10/1970 |
| JP | 52-048691 | 4/1977 |
| JP | 57-156500 | 9/1982 |
| JP | 59-051213 | 3/1984 |
| JP | 61-227792 | 10/1986 |
| JP | 01-049274 | 10/1989 |
| JP | 01-049275 | 10/1989 |
| JP | 03-501970 | 5/1991 |
| JP | 04-021478 | 1/1992 |
| JP | 06-030607 | 2/1994 |
| JP | 09-077674 | 3/1997 |
| JP | 09-077674 | * 3/1998 |
| JP | 2005-229812 | * 9/2005 |
| WO | WO 89/03389 | 4/1989 |
| WO | WO 91/11509 | 8/1991 |

OTHER PUBLICATIONS

Sonnerat, Isabelle, Extended European Search Report, May 2, 2010, European Patent Office.

Allessandra, Morana, Stabilization of S-adenosyl-L-methionine by trehalose, Jun. 17, 2002, Biochemica et Biophysica Acta, p. 105-108, vol. 1573.

Holcomb et al., "Assay and Regulation of S-Adenosylmethionine Synthetase in *Saccharmyces cerevisiae* and *Candida etilis*", Journal of Bacteriology, vol. 121, No. 1, pp. 267-271, Jan. 1975.

(Continued)

*Primary Examiner* — Iqbal H Chowdhury
(74) *Attorney, Agent, or Firm* — Oblon, McClelland, Maier & Neustadt, L.L.P.

(57) ABSTRACT

A method for producing a dry yeast containing S-adenosyl-L-methionine using a yeast having production capability of S-adenosyl-L-methionine, in which an ascorbic acid compound or a salt thereof is added to a yeast concentrate separated from a fungus culture liquid of the yeast, and the concentrate is then dried, a dry yeast containing SAMe obtained by the production method, and a composition for oral ingestion formed by molding the dry yeast. A method capable of producing a dry yeast containing SAMe in a high concentration excellent in storage stability conveniently at low cost is established, and a dry yeast containing SAMe obtained by the production method and a composition for oral ingestion formed by molding the dry yeast are provided.

11 Claims, 1 Drawing Sheet

(56) References Cited

OTHER PUBLICATIONS

Heick et al., "The occurrence of ascorbic acid among the yeasts", Can. J. Microbial., vol. 18, pp. 597-600, 1972.

Machine translation of JP 09-077674.
Machine translation of JP 2005-229812.

* cited by examiner

METHOD OF PRODUCING S-ADENOSYL-L-METHIONINE-CONTAINING DRY YEAST HAVING EXCELLENT STORAGE STABILITY, THE PRODUCT THEREOF AND COMPOSITION FOR ORAL INTAKE

TECHNICAL FIELD

The present invention relates to a method for producing a dry yeast containing S-adenosyl-L-methionine excellent in storage stability, using a yeast having production capability of S-adenosyl-L-methionine (which is hereinafter described as SAMe), and a product produced by the production method. More specifically, it relates to a method for producing a dry yeast containing SAMe excellent in storage stability, using a yeast having production capability of the SAMe, in which an ascorbic acid compound or a salt thereof is added to a yeast concentrate obtained from a fungus culture liquid of the yeast, and then the concentrate is dried, and to a dry yeast containing SAMe obtained by the production method, and a composition for oral ingestion formed by molding the dry yeast containing SAMe.

BACKGROUND ART

SAMe is a water soluble physiologically active substance that plays an important role as a methyl group donor in methylation reaction with various transmethylases within the living body, is found in most of cells in the human body, functions as a cofactor of various biochemical reactions, and is a substance that is necessary, for example, for maintenance of cartilage and biosynthesis of brain substances. Studies on functions of SAMe in recent years report curative effects on fatty liver, hyperlipemia, arteriosclerosis, insomnia and the like. SAMe is an important physiologically active substance and is widely used in the Western countries as a therapeutic medication for depression, liver disorder, arthritis and the like, or health foods.

Accordingly, there are strong demands on production and provision of SAMe at low cost with ease, and the known production methods of SAMe include a method of fermentative production using a culture medium containing L-methionine as a precursor (see, for example, Patent Documents 1 to 3 and Non-patent Documents 1 to 7), a method of enzymatically synthesizing SAMe with adenosine 5'-triphosphate (ATP) and L-methionine as substrates using a SAMe synthesizing enzyme (methionine adenosyltransferase), which is isolated and purified from microorganisms, such as a yeast (see, for example, Patent Document 4 and Non-patent Documents 7 to 11), and a method of synthesis process (see, for example, Patent Document 5 and Non-patent Document 12).

In the enzymatic synthesis method, SAMe is enzymatically synthesized with adenosine 5'-triphosphate (ATP) and L-methionine as substrates using a SAMe synthesizing enzyme (methionine adenosyltransferase), which is isolated and purified from microorganisms, such as a yeast, and the method has such advantages that SAMe is accumulated in a large amount, and it is not necessary to extract SAMe from the fungus, as compared to the fermentative method, but has various problems, in which preparation of the enzyme is complicated, the resulting enzyme has weak activity, inhibition enzyme activity, such as ATP degradation activity, is necessarily removed, and ATP as the substrate is considerably expensive, and therefore, the method has not been subjected to practical use.

According to developments of gene engineering in recent years, the enzyme can be conveniently prepared by using cloned SAMe synthesizing enzyme gene (see, for example, Non-patent Documents 6 to 9) to solve the problem in preparation of the enzyme, but other practical problems, such as the use of expensive ATP as the substrate, have not yet been resolved.

Furthermore, SAMe is thermally unstable and is easily decomposed, and as a countermeasure thereto, various attempts have been made for improving the storage stability. For example, such a method is generally employed that a composition of SAMe obtained by the aforementioned methods is purified through chromatography or the like, and formed into a salt with sulfuric acid or p-toluenesulfonic acid, a salt with butanesulfonic acid, or the like, thereby stabilizing SAMe (see, for example, Patent Documents 1 to 3 and 6 to 10), but large amounts of labor and cost are required therefor, and it is difficult to produce and provide SAMe, which is important as a therapeutic medication and health foods and excellent in storage stability, at low cost.

[Patent Document 1] JP-B-4-21478
[Patent Document 2] JP-B-6-30607
[Patent Document 3] European Patent No. 1,091,001
[Patent Document 4] JP-A-61-227792
[Patent Document 5] U.S. Pat. No. 6,881,837
[Patent Document 6] JP-A-59-51213
[Patent Document 7] JP-A-52-48691
[Patent Document 8] JP-B-1-49274
[Patent Document 9] JP-B-1-49275
[Patent Document 10] JP-T-3-501970
[Non-patent Document 1] Schlenk F., DePalma R. E., J. Biol. Chem., 229, 1037-1050 (1957)
[Non-patent Document 2] Shiozaki S., et al, Agric. Biol. Chem., 48, 2293-2300 (1984)
[Non-patent Document 3] Shiozaki S., et al, Agric. Biol. Chem., 53, 3269-3274 (1989)
[Non-patent Document 4] Kusakabe H., Kuninaka A., Yoshino H., Agric. Biol. Chem., 38, 1669-1672 (1974)
[Non-patent Document 5] Mudd S H., Cantoni G L., et al, J. Biol. Chem., 231, 481-492 (1958)
[Non-patent Document 6] Shiozaki S., et al, J. Biotechnology., 4, 345-354 (1986)
[Non-patent Document 7] Thomas D., Surdin-Kerjan Y., J. Biol. Chem., 262, 16704-16709 (1987)
[Non-patent Document 8] Markham G. D., et al, J. Biol. Chem., 255, 9082-9092 (1980)
[Non-patent Document 9] Markham D J., DeParisis J., J. Biol. Chem., 259, 14505-14507 (1984)
[Non-patent Document 10] Thomas D., Cherest H., et al, Mol. Cell. Biol., 8, 5132-5139 (1988)
[Non-patent Document 11] Jeongho Park, Junzhe Tai, Charles A. Roessner and A. Ian Scott., Bioorganic & Medical Chemistry, Vol. 4, No. 12, 2179-2185 (1996)
[Non-patent Document 12] Jose R. Mator, Frank M. Raushel, Chi-Huey Wong., Biotechnology and Applied Biochemistry., 9, 39-52 (1987)

DISCLOSURE OF THE INVENTION

An object of the present invention is to establish a method capable of producing conveniently a dry yeast containing SAMe in a high concentration excellent in storage stability at low cost, and to provide a dry yeast containing SAMe obtained by the production method and a composition for oral ingestion formed by molding the dry yeast.

As a result earnest investigations made by the inventors with respect to a method capable of producing economically a composition that contains SAMe at a high concentration, can be stored in a stable state for a prolonged period of time, and is excellent in performance, it has been found that the target SAMe-containing dry yeast that contains SAMe in a high concentration and is excellent in storage stability can be produced conveniently at low cost with a high yield in the following manner. A yeast having SAMe production capability capable of being orally ingested is used to synthesize SAMe, which is accumulated in a high concentration in the fungus. The yeast is then separated from the culture liquid with a separation measure, such as centrifugation, and an ascorbic acid compound or a salt thereof is added to the resulting concentrate of the yeast, which is then dried. Consequently, the present invention has been completed.

Accordingly, the present invention provides a method for producing a dry yeast containing SAMe in a high concentration excellent in storage stability, a SAMe-containing dry yeast obtained by the production method, and a composition for oral ingestion formed by molding the dry yeast, shown in the items (1) to (8) below.

(1) A method for producing a dry yeast containing S-adenosyl-L-methionine using a yeast having production capability of S-adenosyl-L-methionine, in which an ascorbic acid compound or a salt thereof is added to a yeast concentrate separated from a fungus culture liquid of the yeast, and the concentrate is then dried.

(2) The method for producing a dry yeast containing S-adenosyl-L-methionine according to the item (1), wherein a yeast belonging to *Saccharomyces* is used as the yeast having production capability of S-adenosyl-L-methionine.

(3) The method for producing a dry yeast containing S-adenosyl-L-methionine according to the item (2), wherein the yeast belonging to *Saccharomyces* is *Saccharomyces cerevisiae*.

(4) The method for producing a dry yeast containing S-adenosyl-L-methionine according to the item (1), wherein the ascorbic acid compound or a salt thereof added is ascorbic acid, an ascorbic acid derivative or salts thereof.

(5) The method for producing a dry yeast containing S-adenosyl-L-methionine according to the item (1), wherein the ascorbic acid compound or a salt thereof added is L-ascorbic acid or sodium L-ascorbate.

(6) The method for producing a dry yeast containing S-adenosyl-L-methionine according to the item (1), wherein an addition amount of the ascorbic acid compound or a salt thereof is in a range of from 0.05 to 5 times by mol S-adenosyl-L-methionine contained in the yeast concentrate.

(7) A dry yeast containing S-adenosyl-L-methionine produced by the method according to one of the items (1) to (6).

(8) A composition for oral ingestion containing the dry yeast containing S-adenosyl-L-methionine according to the item (7), having been molded.

BEST MODE FOR CARRYING OUT THE INVENTION

Figure 1:
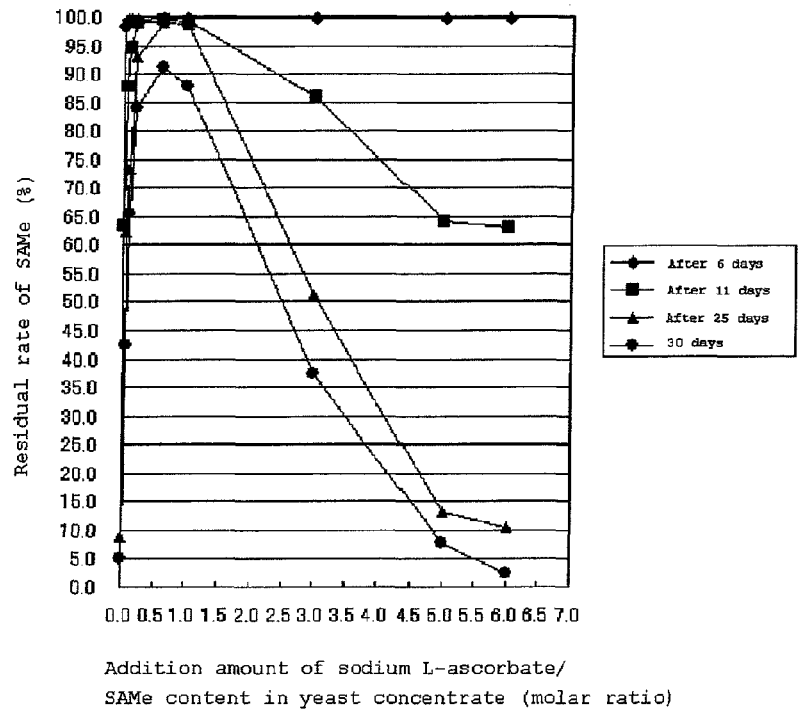
FIG. 1. The figure shows the relationship between the addition amount (molar ratio) of sodium L-ascorbate to SAMe in the yeast concentrate and the residual rate of SAMe in the dry yeast, in the storage stability test under an acceleration condition of 40° C. and 75% RH (relative humidity) in a sealed glass vessel.

The kind of the yeast used in the present invention may be one having production capability of SAMe and capable of being orally ingested, and preferred examples thereof include yeasts belonging to *Saccharomyces*. Among these, *Saccharomyces cerevisiae*, such as fermentation yeast, e.g., sake yeast, baker yeast, beer yeast and wine yeast, is more preferred, and in particular, sake yeast is further preferred. The yeast contains large amounts of useful components, such as 5'-nucleotide, a free amino acid, glutathione having antioxidant action and capability of improving hepatic function, β-glucan having function of enhancing immune strength and function of regulating intestinal function, and dietary fibers, and is used widely as health foods.

A carbon source used for culturing the yeast is not particularly limited as far as it is capable of being utilized by the yeast, and examples thereof include a hydrocarbon, such as glucose, sucrose, starch and blackstrap molasses, an alcohol, such as ethanol, and an organic acid, such as acetic acid. A nitrogen source therefor is also not particularly limited as far as it is capable of being utilized by the yeast, and examples thereof include an inorganic nitrogen compound, such as ammonia, nitric acid and urea, and those containing an organic nitrogen compound, such as yeast extract and malt extract. Examples of an inorganic salt therefor include salts of a phosphoric acid, potassium, sodium, magnesium, calcium, iron, zinc, manganese, cobalt, copper and molybdenum. Furthermore, the culture may be performed by adding methionine, adenine and adenosyl ribonucleoside constituting the skeleton of SAMe.

While the culture temperature and the pH of the culture liquid vary depending on the kind of the yeast, the culture temperature may be in a range of from 20 to 35° C., and the pH of the culture liquid may be in a range of from 4 to 7.

Aerobic culture is preferred for increasing the SAMe content in the fungus. The culture vessel is preferably aerated and can be stirred depending on necessity, and for example, a mechanically stirred culture vessel, an air-lift type culture vessel, a bubble tower type culture vessel and the like may be used.

The culture components, such as the carbon source, the nitrogen source, the various inorganic salts and various additives, may be added to the culture vessel at one time or individually and continuously or intermittently. For example, the substrate, such as sucrose and ethanol, may be fed to the culture vessel in the form of a mixture with other components of the culture medium, or may be independently added to the culture vessel separately from the other components of the culture medium. The pH of the culture liquid can be controlled with an acid or alkali solution. The alkali for controlling the pH is preferably ammonia and urea, which are used as the nitrogen source, or a non-nitrogen base, such as sodium hydroxide and potassium hydroxide. Examples of the acid used include an inorganic acid, such as phosphoric acid, sulfuric acid and nitric acid, and an organic acid. A phosphate salt, a potassium salt, a sodium salt, a nitrate salt and the like, which are inorganic base, may be used for controlling the pH.

The yeast is cultured under the conditions, and in the stage where the target amount of SAMe is accumulated in the yeast, the culture liquid is taken out from the culture vessel and then separated to provide a yeast concentrate. The separating method is not particularly limited as far as the fungus can be separated and rinsed efficiently, and preferred examples thereof include a counter current yeast separator and an ultrafiltration apparatus using a separation membrane.

An ascorbic acid compound or a salt thereof is added to the yeast concentrate thus separated. Accordingly, SAMe in the dry yeast is improved in storage stability, and the yield of the yeast in the drying step is also improved.

Examples of the ascorbic acid compound or a salt thereof used in the present invention include ascorbic acid or a salt thereof, and an ascorbic acid derivative or a salt thereof.

Examples of ascorbic acid or a salt thereof include L-ascorbic acid, an alkali metal salt thereof, such as sodium L-ascorbate and potassium L-ascorbate, and an alkaline earth metal salt thereof, such as calcium L-ascorbate. Examples of the ascorbic acid derivative or a salt thereof include ascorbic acid 2-glucoside, ascorbic acid phosphate ester, ascorbic acid palmitate ester, ascorbic acid stearate ester and salts thereof. Among these, ascorbic acid and a salt thereof are preferred, L-ascorbic acid and sodium L-ascorbate are more preferred, and sodium L-ascorbate is particularly preferred. The ascorbic acid compound or a salt thereof is commonly used as medical drugs and foods in the form of powder, granules or crystals, and can be used safely.

The addition amount of the ascorbic acid compound or a salt thereof is preferably in a range of from 0.05 to 5 times by mol, and more preferably in a range of from 0.1 to 3.5 times by mol, in terms of the molar ratio of the ascorbic acid compound or a salt thereof added, with respect to SAMe contained in the yeast concentrate. In the case where the ratio is less than 0.05 time by mol, the storage stability of SAMe in the dry yeast may be insufficient, and in the case where it exceeds 5 times by mol, not only it is needless, but also the storage stability of SAMe in the dry yeast per the addition amount tends to be lowered. Furthermore, the addition amount of sodium L-ascorbate is further preferably in a range of from 0.1 to 3.0 times by mol, and particularly preferably in a range of from 0.2 to 1.0 time by mol, in terms of the molar ratio with respect to SAMe contained in the yeast concentrate. The addition amount of L-ascorbic acid is particularly preferably in a range of from 1.8 to 3.1 times by mol in terms of the molar ratio, the addition amount of calcium L-ascorbate is particularly preferably in a range of from 0.3 to 1.9 times by mol in terms of the molar ratio, and the addition amount of potassium L-ascorbate is particularly preferably in a range of from 1.5 to 3.5 times by mol in terms of the molar ratio.

The SAMe-containing dry yeast can be stored stably for a prolonged period of time by adding sulfuric acid and the ascorbic acid compound or a salt thereof in combination to the yeast concentrate separated from the fungus culture liquid. In this case, the combination of the addition amount of sulfuric acid and the addition amount of the ascorbic acid compound or a salt thereof is preferably an addition amount of sulfuric acid providing pH of from 2 to 4 for the yeast concentrate separated from the fungus culture liquid and an addition amount of the ascorbic acid compound or a salt thereof providing a molar ratio of the ascorbic acid compound or a salt thereof in a range of from 0.5 to 3.0 times by mol in terms of the molar ratio thereof with respect to SAMe contained in the yeast concentrate, more preferably an addition amount of sulfuric acid providing pH of from 2 to 3 therefor and an addition amount of the ascorbic acid compound or a salt thereof in a range of from 1.0 to 2.0 times by mol in terms of the molar ratio, and further preferably an addition amount of sulfuric acid providing pH of from 2 to 3 therefor and an addition amount of the ascorbic acid compound or a salt thereof in a range of from 1.0 to 1.7 times by mol in terms of the molar ratio.

After adding the ascorbic acid compound or a salt thereof, the water content of the resulting yeast concentrate is evaporated, for example, by such a drying method as a spray drying method with a spray dryer and a freeze drying method, thereby providing a dry yeast. In the spray drying method, the concentrate is preferably dried at an inlet temperature of 210° C. or less and an outlet temperature of 110° C. or less. In the freeze drying method, the concentrate is preferably dried at a final stage temperature of 30° C. The composition for oral ingestion containing SAMe of the present invention preferably has a water content of 5.0% by mass or less from the standpoint of storage stability thereof.

Furthermore, the dry yeast may be pulverized to powder, and another bioactive component and an additive, such as a vehicle, may be added to the dry yeast in the form of powder if needed, which may be then tabletted by compression to provide a composition for oral ingestion in the form of tablet. The surface of the tablet may be coated. The powder may be granulated into a granular form, and the powder or the granules thus granulated may be capsulated.

EXAMPLE

The present invention will be described in more detail with reference to examples and comparative examples, but the present invention is not limited to the examples.

Examples 1 to 8

(a) Culture of Yeast

According to the known culture method (Schlenk F., DePalma R. E., J. Biol. Chem., 229, 1037-1050 (1957) (Non-patent Document 1) and Shiozaki S., et al, Agric. Biol. Chem., 53, 3269-3274 (1989) (Non-patent Document 3)), *Saccharomyces cerevisiae* IFO 2346 belonging to *Saccharomyces* was inoculated in a culture medium containing L-methionine (Shiozaki S. et al, J. Biotechnology, 4, 345-354 (1986) (Non-patent Document 6)), and cultured at a culture temperature of from 27 to 29° C. and stirred under aerophilic aeration for 6 days. Consequently, 18 L of a yeast culture liquid having a fungus content of 3.5% by mass and a SAMe content of 205 mg per gram of dry yeast was obtained.

(b) Collection of Yeast

18 L of the yeast culture liquid was treated with a continuous rotary type centrifugal separator (Hitachi Himac Centrifuge CR10B2) to provide 3.49 kg of a yeast concentrate in the form of liquid having a fungus concentration corresponding to 18% by mass in terms of dry product.

(c) Addition of Ascorbic Acid Compound or Salt Thereof to Yeast Concentrate

Sodium L-ascorbate was added to 3.49 kg of the yeast concentrate in an amount of 0.05, 0.1, 0.2, 0.6, 1.0, 3.0, 5.0 or 6.0 times by mol SAMe in the yeast concentrate, and dissolved under stirring at room temperature for 30 minutes, thereby providing a yeast concentrate having sodium L-ascorbate added thereto.

(d) Production of Dry Yeast

Figure 2:
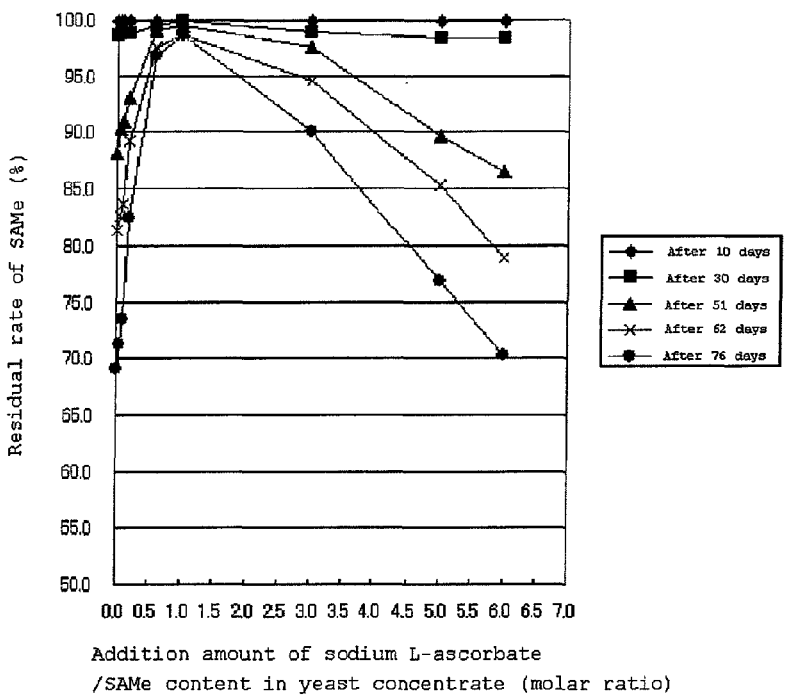
FIG. 2. The figure shows the relationship between the addition amount (molar ratio) of sodium L-ascorbate to SAMe in the yeast concentrate and the residual rate of SAMe in the dry yeast, in the storage stability test under a temperature condition of 30° C. in a sealed glass vessel.

The yeast concentrate having sodium L-ascorbate added thereto was poured into a stainless steel tray for freeze drying of a freeze dryer (produced by ULVAC, Inc.) and frozen at −50° C., and then freeze dried for 36 hours under conditions of a final stage temperature of 25° C. The resulting freeze dried yeast was further pulverized to provide a powder dry yeast. The powder dry yeast thus obtained was charged in a sealed glass vessel and tested for storage stability under an acceleration condition of 40° C. and 75% RH or under a temperature condition of 30° C. The results for 40° C. and 75% RH are shown in Table 1 (Examples 1-1 to 8-1) and FIG. 1, and the results for 30° C. are shown in Table 2 (Examples 1-2 to 8-2) and FIG. 2. The SAMe contents of the resulting powder yeasts are shown in Tables 1 and 2.

The residual rate of SAMe was measured in such a manner that SAMe was extracted from the SAMe-containing dry yeast by a known method using perchloric acid (see, for example, Non-patent Document 2) and quantitatively determined with liquid chromatography. The liquid chromatography was performed under the following analysis conditions.
Column: Nacalai Tesque, Inc., Cosmosil 4.6 mm in diameter × 100 mm
Eluant: 0.2M $KH_2PO_4$ aqueous solution/methanol=95/5 (volume ratio)
Flow rate: 0.7 mL/min
Detector: UV (260 nm)
SAMe retention time: ca. 150 seconds Examples 9 to 12

Powder dry yeasts were obtained in the same manner as in Example 1 except that L-ascorbic acid was added to the yeast concentrate in an amount of 0.6, 1.8, 3.1 or 4.3 times by mol SAMe in the yeast concentrate. The results of the storage stability test of the resulting SAMe-containing dry yeasts in a sealed glass vessel under an acceleration condition of 40° C. and 75% RH are shown in Table 1 (Examples 9-1 to 12-1), and the results of the storage stability test under a temperature condition of 30° C. are shown in Table 2 (Examples 9-2 to 12-2). The SAMe contents of the resulting powder yeasts are shown in Tables 1 and 2.

Examples 13 to 17

Powder dry yeasts were obtained in the same manner as in Example 1 except that calcium L-ascorbate was added to the yeast concentrate in an amount of 0.3, 0.8, 1.4, 1.9 or 2.5 times by mol SAMe in the yeast concentrate. The SAMe contents of the resulting powder yeasts and the results of the storage stability test of the resulting powder yeasts in a sealed glass vessel under an acceleration condition of 40° C. and 75% RH are shown in Table 1 (Examples 13-1 to 17-1).

Examples 18 to 22

Powder dry yeasts were obtained in the same manner as in Example 1 except that potassium L-ascorbate was added to the yeast concentrate in an amount of 0.5, 1.5, 2.5, 3.5 or 4.5 times by mol SAMe in the yeast concentrate. The SAMe contents of the resulting powder yeasts and the results of the storage stability test of the resulting powder dry yeasts in a sealed glass vessel under an acceleration condition of 40° C. and 75% RH are shown in Table 1 (Examples 18-1 to 22-1).

Examples 23 and 24

The operations (a) to (b) were performed in the same manner as in Example 1, and L-ascorbic acid or sodium L-ascorbate was added to the resulting liquid yeast concentrate in an amount of 1.0 time SAMe contained in the yeast concentrate and dissolved by stirring at room temperature for 30 minutes, thereby providing a yeast concentrate having L-ascorbic acid or sodium L-ascorbate dissolved therein.

The yeast was spray dried with a spray dryer having a two-fluid nozzle as an apparatus for being turned into fine particles under a condition of an inlet temperature of the drying chamber of 145° C., an outlet temperature thereof of 85° C. and a liquid feeding rate of 1.5 g/min to provide a powder dry yeast. The SAMe contents of the resulting powder yeasts and the results of the storage stability test of the resulting SAMe-containing powder dry yeasts in a sealed glass vessel under an acceleration condition of 40° C. and 75% RH are shown in Table 3 (Examples 23-1 and 24-1).

Comparative Example 1

A powder dry yeast was obtained in the same manner as in Example 1 except that the ascorbic acid compound or a salt thereof was not added to the yeast concentrate. The SAMe content of the resulting powder yeast is shown in Tables 1 and 2. The results of the storage stability test of the resulting SAMe-containing powder dry yeast in a sealed glass vessel under an acceleration condition of 40° C. and 75% RH are shown in Table 1 (Comparative Example 1-1) and FIG. 1. The results of the storage stability test under a temperature condition of 30° C. are shown in Table 2 (Comparative Example 1-2) and FIG. 2.

Comparative Example 2

A powder dry yeast was obtained in the same manner as in Example 1 except that citric acid was added to the yeast concentrate in an amount of 2.8 equivalents in terms of molar ratio with respect to SAMe in the yeast concentrate. The SAMe content of the resulting powder yeast and the results of the storage stability test of the resulting SAMe-containing powder dry yeast in a sealed glass vessel under an acceleration condition of 40° C. and 75% RH are shown in Table 1 (Comparative Example 2-1).

Comparative Example 3

A powder dry yeast was obtained in the same manner as in Example 1 except that EDTA was added to the yeast concentrate in an amount of 1.9 equivalents in terms of molar ratio with respect to SAMe in the yeast concentrate. The SAMe content of the resulting powder yeast and the results of the storage stability test of the resulting SAMe-containing powder dry yeast in a sealed glass vessel under an acceleration condition of 40° C. and 75% RH are shown in Table 1 (Comparative Example 3-1).

Examples 25 to 35

Powder dry yeasts were obtained in the same manner as in Example 1 except that in the operation of (c), sulfuric acid was added to the yeast concentrate obtained in (b) to make pH of 2, 3 or 4, and sodium L-ascorbate was then added in an amount of 0.6, 1.0, 1.7, 2.8 or 3.9 times by mol SAMe in the yeast concentrate. The SAMe contents of the resulting powder yeasts and the results of the storage stability test of the resulting powder dry yeasts in a sealed glass vessel under an acceleration condition of 40° C. and 75% RH are shown in Table 4 (Examples 25-1 to 35-1).

Table 1: Results of storage stability test of SAMe-containing dry yeasts in sealed glass vessel under acceleration condition of 40° C. and 75% RH

TABLE 1

| Example | Addition amount of additive* to yeast concentrate (g) | Added molar ratio of additive* to SAMe in yeast concentrate | SAMe content in dry yeast at start of test (mg/g of dry yeast) | Storage stability test SAMe residual rate in SAMe-containing yeast (%) Elapsed days | | | |
|---|---|---|---|---|---|---|---|
| | | | | After 6 days | After 11 days | After 25 days | After 30 days |
| Comparative Example 1-1 | 0.0 | 0.0 | 136.2 | 98.3 | 63.4 | 9.0 | 5.1 |
| Example 1-1 | 3.2 | 0.05 | 140.4 | 99.4 | 87.9 | 62.3 | 42.6 |
| Example 2-1 | 6.4 | 0.1 | 144.6 | 99.4 | 94.5 | 73.2 | 65.4 |
| Example 3-1 | 12.8 | 0.2 | 154.4 | 99.5 | 98.8 | 93.1 | 84.2 |
| Example 4-1 | 38.3 | 0.6 | 169.5 | 99.7 | 99.4 | 98.9 | 91.2 |
| Example 5-1 | 63.9 | 1.0 | 157.7 | 99.6 | 99.3 | 98.6 | 87.8 |
| Example 6-1 | 191.6 | 3.0 | 139.8 | 99.7 | 85.9 | 51.3 | 37.6 |
| Example 7-1 | 319.4 | 5.0 | 137.9 | 99.6 | 64.1 | 13.3 | 7.9 |
| Example 8-1 | 384.0 | 6.0 | 137.0 | 99.6 | 63.1 | 10.5 | 2.5 |
| Example 9-1 | 12.8 | 0.6 | 142.8 | 98.8 | 79.2 | 17.1 | 4.7 |
| Example 10-1 | 38.3 | 1.8 | 147.1 | 98.9 | 92.1 | 87.1 | 9.0 |
| Example 11-1 | 63.9 | 3.1 | 147.4 | 98.4 | 90.4 | 87.7 | 6.4 |
| Example 12-1 | 191.6 | 4.3 | 149.6 | 98.8 | 75.4 | 7.5 | 0.0 |
| Example 13-1 | 34.9 | 0.3 | 140.4 | 99.1 | 88.2 | 54.5 | 21.7 |
| Example 14-1 | 104.7 | 0.8 | 147.0 | 100.0 | 94.6 | 69.9 | 34.8 |
| Example 15-1 | 174.5 | 1.4 | 147.0 | 99.3 | 93.2 | 63.8 | 28.6 |
| Example 16-1 | 244.3 | 1.9 | 140.0 | 100.0 | 98.6 | 49.5 | 15.0 |
| Example 17-1 | 314.1 | 2.5 | 138.1 | 100.0 | 92.8 | 26.5 | 2.9 |
| Example 18-1 | 34.9 | 0.5 | 144.0 | 99.7 | 89.1 | 30.9 | 0.0 |
| Example 19-1 | 104.7 | 1.5 | 151.0 | 99.8 | 95.2 | 66.7 | 30.6 |
| Example 20-1 | 174.5 | 2.5 | 157.0 | 99.7 | 97.5 | 68.7 | 28.6 |
| Example 21-1 | 244.3 | 3.5 | 150.0 | 99.8 | 97.8 | 72.9 | 30.7 |
| Example 22-1 | 314.1 | 4.5 | 138.1 | 99.7 | 76.1 | 32.6 | 2.9 |
| Comparative Example 2-1 | 174.5 | 2.8 | 153.4 | 99.4 | 91.8 | 32.9 | 28.3 |
| Comparative Example 3-1 | 174.5 | 1.9 | 155.3 | 99.3 | 78.3 | 11.3 | 0.0 |

Examples 1-1 to 8-1: sodium L-ascorbate added (drying method: freeze drying)

Examples 9-1 to 12-1: L-ascorbic acid added (drying method: freeze drying)

Examples 13-1 to 17-1: calcium L-ascorbate added (drying method: freeze drying)

Examples 18-1 to 22-1: potassium L-ascorbate added (drying method: freeze drying)

Comparative Example 2-1: citric acid added (drying method: freeze drying)

Comparative Example 3-1: EDTA added (drying method: freeze drying)

Table 2: Results of storage stability test of SAMe-containing dry yeasts in sealed glass vessel under temperature condition of 30° C.

TABLE 2

| Example | Addition amount of additive* to yeast concentrate (g) | Added molar ratio of additive* to SAMe in yeast concentrate | SAMe content in dry yeast at start of test (mg/g of dry yeast) | Storage stability test SAMe residual rate in SAMe-containing yeast (%) Elapsed days | | | | |
|---|---|---|---|---|---|---|---|---|
| | | | | After 10 days | After 30 days | After 51 days | After 62 days | After 76 days |
| Comparative Example 1-2 | 0.0 | 0.0 | 136.2 | 99.8 | 98.7 | 88.2 | 81.4 | 69.1 |
| Example 1-2 | 3.2 | 0.05 | 140.4 | 99.8 | 98.8 | 90.3 | 82.6 | 71.3 |
| Example 2-2 | 6.4 | 0.1 | 144.6 | 99.8 | 98.8 | 91.0 | 83.7 | 73.4 |
| Example 3-2 | 12.8 | 0.2 | 154.4 | 99.8 | 98.8 | 93.1 | 89.2 | 82.4 |
| Example 4-2 | 38.3 | 0.6 | 169.5 | 99.8 | 99.5 | 99.1 | 97.6 | 96.7 |
| Example 5-2 | 63.9 | 1.0 | 157.7 | 99.9 | 99.8 | 99.5 | 98.7 | 98.6 |
| Example 6-2 | 191.6 | 3.0 | 139.8 | 99.8 | 98.9 | 97.6 | 94.6 | 90.1 |
| Example 7-2 | 319.6 | 5.0 | 137.9 | 99.8 | 98.4 | 89.7 | 85.3 | 76.8 |
| Example 8-2 | 384.0 | 6.0 | 137.0 | 99.8 | 98.4 | 86.5 | 78.9 | 70.3 |
| Example 9-2 | 12.8 | 0.6 | 142.8 | 99.8 | 99.1 | 91.3 | 88.3 | 74.5 |
| Example 10-2 | 38.3 | 1.8 | 147.1 | 99.9 | 98.8 | 91.2 | 87.3 | 73.1 |
| Example 11-2 | 63.9 | 3.1 | 147.4 | 99.8 | 98.7 | 89.9 | 86.3 | 72.8 |
| Example 12-2 | 191.6 | 4.3 | 149.6 | 99.8 | 99.0 | 88.5 | 84.9 | 70.4 |

Examples 1-2 to 8-2: sodium L-ascorbate added (drying method: freeze drying)

Examples 9-2 to 12-2: L-ascorbic acid added (drying method: freeze drying)

Table 3: Results of storage stability test of SAMe-containing dry yeasts in sealed glass vessel under acceleration condition of 40° C. and 75% RH

TABLE 3

| Example | Addition amount of additive* to yeast concentrate (g) | Added molar ratio of additive* to SAMe in yeast concentrate | SAMe content in dry yeast at start of test (mg/g of dry yeast) | Storage stability test SAMe residual rate in SAMe-containing yeast (%) Elapsed days | | |
|---|---|---|---|---|---|---|
| | | | | After 14 days | After 28 days | After 35 days |
| Comparative Example 1-1 | 0.0 | 0.0 | 136.2 | 54.3 | 6.7 | 0.0 |
| Example 5-1 | 63.9 | 1.0 | 157.7 | 99.2 | 88.7 | 80.3 |
| Example 9-1 | 12.8 | 0.6 | 142.8 | 74.3 | 13.9 | 3.4 |
| Example 10-1 | 38.3 | 1.8 | 147.1 | 86.3 | 81.3 | 5.2 |
| Example 23-1 | 63.9 | 1.0 | 156.7 | 99.8 | 99.7 | 82.8 |
| Example 24-1 | 21.3 | 1.0 | 154.5 | 88.9 | 82.3 | 53.6 |

Comparative Example 1-1: not added (drying method: freeze drying)
Example 3-1: sodium L-ascorbate added (drying method: freeze drying)
Examples 9-1 and 10-1: L-ascorbic acid added (drying method: freeze drying)
Example 23-1: sodium L-ascorbate added (drying method: spray drying)
Example 24-1: L-ascorbic acid added (drying method: spray drying)

Table 4: Results of storage stability test of SAMe-containing dry yeasts in sealed glass vessel under acceleration condition of 40° C. and 75% RH in case of using sulfuric acid and sodium L-ascorbate in combination

TABLE 4

| Example | pH after adding sulfuric acid | Addition amount of sodium ascorbate to yeast concentrate (g) | Added molar ratio of sodium ascorbate to SAMe in yeast concentrate | SAMe content in dry yeast at start of test (mg/g of dry yeast) | Storage stability test SAMe residual rate in SAMe-containing yeast (%) Elapsed days | | | | | | |
|---|---|---|---|---|---|---|---|---|---|---|---|
| | | | | | After 12 days | After 20 days | After 28 days | After 45 days | After 60 days | After 75 days | After 95 days |
| Example 25-1 | 2 | 35.8 | 0.6 | 178.2 | 97.5 | 97.4 | 96.3 | 89.7 | 78.6 | 65.2 | 45.8 |
| Example 26-1 | 2 | 64.0 | 1.0 | 168.2 | 99.7 | 99.5 | 98.9 | 95.7 | 85.7 | 73.6 | 52.8 |
| Example 27-1 | 2 | 106.9 | 1.7 | 160.6 | 99.5 | 99.4 | 98.7 | 95.2 | 84.1 | 71.5 | 50.1 |
| Example 28-1 | 2 | 177.9 | 2.8 | 143.3 | 93.4 | 86.3 | 76.4 | 63.8 | 50.2 | 39.5 | 15.3 |
| Example 29-1 | 2 | 249.6 | 3.9 | 130.7 | 89.4 | 80.2 | 71.3 | 62.1 | 49.0 | 35.2 | 12.8 |
| Example 30-1 | 3 | 35.8 | 0.6 | 145.2 | 86.5 | 82.3 | 77.6 | 65.4 | 52.3 | 32.5 | 10.0 |
| Example 31-1 | 3 | 64.0 | 1.0 | 161.9 | 98.4 | 98.5 | 97.2 | 91.0 | 83.5 | 69.8 | 48.2 |
| Example 32-1 | 3 | 106.9 | 1.7 | 157.8 | 98.8 | 98.6 | 97.4 | 91.2 | 80.3 | 67.9 | 47.5 |
| Example 33-1 | 3 | 177.9 | 2.8 | 145.2 | 98.7 | 98.1 | 97.1 | 90.6 | 75.1 | 60.2 | 39.2 |
| Example 34-1 | 4 | 64.0 | 1.0 | 151.7 | 98.9 | 89.4 | 77.9 | 64.9 | 55.6 | 30.1 | 14.2 |
| Example 35-1 | 4 | 106.9 | 1.7 | 145.3 | 97.9 | 87.4 | 76.3 | 63.2 | 56.1 | 31.2 | 14.6 |

INDUSTRIAL APPLICABILITY

By using the production method of the present invention, a dry yeast containing SAMe in a high concentration capable of being stored stably and a composition for oral ingestion formed by molding the same can be produced in a convenient manner. Accordingly, SAMe useful as a physiologically active substance for medical drugs and health foods can be provided thereby at an economically cost.

The invention claimed is:

1. A method for producing a dry yeast containing S-adenosyl-L-methionine, the dry yeast having excellent storage stability of S-adenosyl-L-methionine, the method using a yeast having production capability of S-adenosyl-L-methionine, in which a combination of sulfuric acid and an ascorbic acid compound or a salt thereof is added to a yeast concentrate separated from a fungus culture liquid of the yeast, and the concentrate is then dried, wherein an addition amount of the ascorbic acid compound or a salt thereof is in a range of from 0.6 to 2.8 times by mol S-adenosyl-L-methionine contained in the yeast concentrate.

2. The method for producing a dry yeast containing S-adenosyl-L-methionine as claimed in claim 1, wherein a yeast belonging to *Saccharomyces* is used as the yeast having production capability of S-adenosyl-L-methionine.

3. The method for producing a dry yeast containing S-adenosyl-L-methionine as claimed in claim 2, wherein the yeast belonging to *Saccharomyces* is *Saccharomyces cerevisiae*.

4. The method for producing a dry yeast containing S-adenosyl-L-methionine as claimed in claim 1, wherein the ascorbic acid compound or a salt thereof added is ascorbic acid, an ascorbic acid derivative or salts thereof.

5. The method for producing a dry yeast containing S-adenosyl-L-methionine as claimed in claim 1, wherein the ascorbic acid compound or a salt thereof added is L-ascorbic acid or sodium L-ascorbate.

6. The method for producing a dry yeast containing S-adenosyl-L-methionine as claimed in claim 1, wherein the ascorbic acid compound or a salt thereof added is sodium L-ascorbate.

7. The method for producing a dry yeast containing S-adenosyl-L-methionine as claimed in claim 1, wherein the ascorbic acid compound or a salt thereof added is L-ascorbic acid and an addition amount of the L-ascorbic acid is in a range of from 1.8 to 2.8 times by mol S-adenosyl-L-methionine contained in the yeast concentrate.

8. The method for producing a dry yeast containing S-adenosyl-L-methionine as claimed in claim 1, wherein the ascorbic acid compound or a salt thereof added is calcium L-ascorbate and an addition amount of the calcium L-ascorbate is in a range of from 0.6 to 1.9 times by mol S-adenosyl-L-methionine contained in the yeast concentrate.

9. The method for producing a dry yeast containing S-adenosyl-L-methionine as claimed in claim 1, wherein the ascorbic acid compound or a salt thereof added is potassium L-ascorbate and an addition amount of the potassium L-ascorbate is in a range of from 1.5 to 2.8 times by mol S-adenosyl-L-methionine contained in the yeast concentrate.

10. The method for producing a dry yeast containing S-adenosyl-L-methionine as claimed in claim 1, wherein an addition amount of the sulfuric acid provides a pH of from 2 to 4 for the yeast concentrate.

11. The method for producing a dry yeast containing S-adenosyl-L-methionine as claimed in claim 1, wherein an addition amount of the sulfuric acid provides a pH of from 2 to 3 for the yeast concentrate, and the addition amount of the ascorbic acid compound or a salt thereof is in a range of from 1.0 to 2.0 times by mol S-adenosyl-L-methionine contained in the yeast concentrate.

* * * * *